United States Patent [19]

Spiegelman et al.

[11] 4,434,102
[45] Feb. 28, 1984

[54] PREPARATION OF MIXTURES OF METHYLTIN TRICHLORIDE AND DIMETHYLTIN DICHLORIDE FROM STANIC CHLORIDE AND DIMETHYLTIN DICHLORIDE WITHOUT CATALYST AND CONVERSION TO MIXED METHYLTIN MERCAPTIDE STABILIZERS

[75] Inventors: Gerald Spiegelman, Wayne; Koei-Liang Liauw, Wyckoff, both of N.J.

[73] Assignee: Witco Chemical Corporation, New York, N.Y.

[21] Appl. No.: 227,899

[22] Filed: Jan. 23, 1981

Related U.S. Application Data

[62] Division of Ser. No. 59,094, Jul. 19, 1979, Pat. No. 4,269,782.

[51] Int. Cl.$^3$ .............................................. C07F 7/22
[52] U.S. Cl. .................................................. 260/429.7
[58] Field of Search ..................................... 260/429.7

[56] References Cited

U.S. PATENT DOCUMENTS

| | | | |
|---|---|---|---|
| 2,731,482 | 1/1956 | Stefl et al. | 260/429.7 |
| 2,731,484 | 1/1956 | Best | 260/429.7 |
| 2,832,750 | 4/1958 | Weinberg et al. | 260/429.7 X |
| 2,870,182 | 1/1959 | Leistner et al. | 260/429.7 |

*Primary Examiner*—Helen M. S. Sneed
*Attorney, Agent, or Firm*—Wallenstein, Wagner, Hattis, Strampel & Aubel

[57] ABSTRACT

A process for making a mixed product of dimethyltin dichloride and methyltin trichloride by reacting dimethyltin dichloride with stannic chloride without catalyst. The mixed product is useful as an intermediate, without further purification, in the preparation of corresponding mercaptide stabilizer for vinyl chloride polymers.

3 Claims, No Drawings

PREPARATION OF MIXTURES OF METHYLTIN TRICHLORIDE AND DIMETHYLTIN DICHLORIDE FROM STANIC CHLORIDE AND DIMETHYLTIN DICHLORIDE WITHOUT CATALYST AND CONVERSION TO MIXED METHYLTIN MERCAPTIDE STABILIZERS

This is a division, of application Ser. No. 059,094, filed July 19, 1979 now U.S. Pat. No. 4,269,782.

BACKGROUND OF THE INVENTION

1. Field of the Invention

This invention relates to mixtures of methyltin trichloride and dimethyltin dichloride in certain proportitons, and to a convenient, industrially practical process for the manufacture of such mixtures of satisfactory quality to be used without purification to make industrially useful mixtures of methyltin and dimethyltin compounds, for example methyltin trimercaptide and dimethyltin dimercaptide stabilizers for vinyl chloride polymers. Descriptive references to these mercaptide stabilizers for halogen-containing polymers are abundantly cited in U.S. Pat. No. 4,134,868, to Minagawa et al, issued on Jan. 16, 1979, and incorporated herein by reference.

2. Prior Art

Dimethyltin dichloride can be prepared by a redistribution reaction of methyltin compound having more than two methyl groups linked to a tin atom, i.e. tetramethyltin and/or trimethyltin chloride, with a tin compound having fewer than two methyl groups linked to a tin atom, i.e. methyltin trichloride and/or stannic chloride, as disclosed, for example by D. Grant et al in Journal of Organometallic Chemistry 1965, vol. 4, pages 229-236, and by E. Van den Berghe et al, ibid. 1966, vol. 6, pages 522-527. According to these references, the following reactions, not requiring the use of a catalyst, lead to a dimethyltin dichloride:

The consumption of tetramethyltin in these reactions is rapidly completed, but trimethyltin chloride is incompletely consumed when the reactions reach equilibrium and no further conversion takes place. The use of the highly toxic tetramethyltin or trimethyltin starting material and unreacted trimethyltin chloride in the finished product is a serious drawback of this procedure. Moreover, the trimethyltin mercaptides formed from mixtures containing trimethyltin chloride are also toxic and can only be tolerated as stabilizers for vinyl chloride polymers at carefully controlled low levels well below 1% by weight of the stabilizer, as disclosed for example by L. Weisfeld et al in U.S. Pat. No. 3,887,519 of June 3, 1975.

As is seen in the above reaction equations, methyltin trichloride can be both formed and consumed in this redistribution reaction. This reaction, however, is not a practical method for manufacturing methyltin trichloride, as is pointed out in the above mentioned Van den Berghe et al article, and it is limited to tetramethyltin and trimethyltin compound starting materials. For example, the disclosure in Weisfeld et al, supra, includes an example of dimethyltin dichloride purification to remove a trimethyltin chloride contaminant by using dimethyltin dichloride containing 5% trimethyltin chloride with 2.6% by weight of stannic chloride for 2 hours at 120° C. The trimethyltin chloride being thus reduced to 0.5% in the dimethyltin dichloride. Weisfeld et al states that this purification treatment follows the reaction equations:

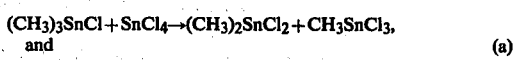
(a)

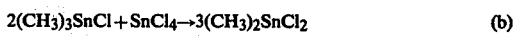
(b)

Calculation shows that a 2.6% SnCl$_4$ addition to a 5.0% (CH$_3$)$_3$ SnCl product can only lower the (CH$_3$)$_3$SnCl content to 1% or less if reaction (b) goes to completion to the exclusion of reaction (a). Accordingly, substantially no methyltin trichloride is formed according to Weisfeld's disclosure.

Langer in U.S. Pat. No. 3,454,610 of July 8, 1969 disclosed the possibility of extending the stannic halide plus alkyltin compound redistribution reaction to the use of disubstituted organometallic halide such as dimethyltin dichloride with stannic chloride, by using as a reaction medium an aliphatic sulfoxide which results in the in situ formation of a sulfoxide complex of the redistribution product. Thus a reaction of 0.05 mole dimethyltin dichloride and 0.05 mole stannic chloride with 0.7 mole dimethyl sulfoxide gave, after precipitation in 1:1 benzene-alcohol, a 90% yield of a white crystalline complex of methyltin trichloride with two moles per mole of methyltin trichloride of dimethyl sulfoxide.

An additional operation of vacuum stripping near room temperature is required, according to Langer, to eliminate dimethyl sulfoxide from the recovered complex and isolate the desired methyltin trichloride.

Neumann in U.S. Pat. No. 3,459,779 of Aug. 5, 1969 disclosed that alkyltin trihalides are obtained from dialkyltin dihalides and tin tetrahalide in the presence of polar substances, particularly phosphorus oxyhalide mixed with phosphoric acid. Isolation of the alkyltin trihalide made by Neumann's process requires fractional distillation to separate the product from excess stannic halide and phosphorus oxyhalide as well as from non-volatile phosphoric acid.

Kugele et al in U.S. Pat. No.3,862,198 of Jan. 21, 1975 disclosed the preparation of alkyltin trihalide from stannic halide and an alkyltin compound having 2, 3, or 4 alkyl groups in the presence of an onium salt catalyst. As onium compounds they disclose compounds of the formula R$_4$ZY where R ia alkyl, aryl, or aralkyl, Z is N, P, or As, and Y is an anion such as halide, sulfate, phosphate, nitrate, acetate, or trihalostannite. Kugele et al warn of a possible decomposition of the desired alkyltin trihalide into alkylhalide and stannous halide, and suggest adding alkyl halide, for example methyl chloride, to suppress this side reaction. There is no disclosure by Kugele et al how to isolate the desired alkyltin trihalide product from the onium salt catalyst. The presence of catalyst in the product contributes to its instability during storage and decreases the effectiveness of the methyltin mercaptide stabilizer prepared therefrom.

A process for the preparation of mixtures of dimethyltin dichloride and monomethyltin trichloride from the reaction of dimethyltin dichloride with stannic chloride, without catalyst, is now developed wherein the disadvantages of the foregoing processes are overcome.

By the present process an intermediate mixture is produced without the formation of unwanted methyl chloride, and said mixture is reacted, without further treatment, with a mercaptan, as known in the art, to produce the corresponding vinyl chloride polymer stabilizers.

SUMMARY OF THE INVENTION

In accordance with the present invention, a product mixture of dimethyltin dichloride and monomethyltin trichloride is prepared by heating under superatmospheric pressure a mixture of dimethyltin dichloride and stannic chloride in the absence of catalyst.

DESCRIPTION OF PREFERRED EMBODIMENTS

The dimethyltin dichloride and stannic chloride are mixed in an autoclave, for instance, using about 0.1 to 0.7 moles of stannic chloride per mole of dimethyltin dichloride, dependent upon the desired composition of the final product. The mixture is heated to a temperature of above about 150° C. and preferably above 170° C. up to about 250° C., under autogenous pressure. If desired, the pressure can be supplemented by the use of an inert gas, such as dry nitrogen, carbon dioxide, or air, for instance, or by the addition of an inert solvent having a boiling point below the reaction temperature, such as heptane, toluene, or xylene, for instance, without adverse effect.

The reaction is continued to completion; the reaction time being dependent on the concentration of stannic chloride and the temperature employed. As little as 5–10 minutes to up to about 50 hours may be required for the reaction to go to completion.

The mixed dimethyltin dichloride-monomethyltin trichloride product is employed, without further purification, as an intermediate to prepare the respective mercaptide stabilizers for vinyl chloride polymers.

In actual operation of the process of this invention, about 90% or more of the stannic chloride is converted to methyltin trichloride, and the product compositions obtained are close to those derived from the reaction equation. For even closer control of the product composition, a modest excess of stannic chloride, suitable 5% of the calculated quantity, can be used and recovered by vacuum stripping at the end of the operation. Alternatively, any desired product composition can be produced by blending appropriate quantities of reaction products having a higher methyltin trichloride content than intended with reaction products having a lower methyltin trichloride content.

The progress of the present reaction can be monitored by sampling the reaction mixture and applying conventional analytical techniques. The consumption of dimethyltin dichloride and formations of methyltin trichloride can be followed, for example by proton magnetic resonance spectroscopy. Unconsumed stannic chloride as well as dimethyltin dichloride and methyltin trichloride product can be detected and estimated in the reaction mixture by treating a sample with an alkylmagnesium halide solution, suitably butylmagnesium chloride, and analyzing the resulting butylmethylstannane derivatives by gas chromatography, as shown in the following reactions.

The equations describe the conversion of the components of the reaction mixture or reaction product to butylstannane derivatives:

$SnCl_4 + 4C_4H_9MgCl$ (excess) $\rightarrow Sn(C_4H_9)_4 4MgCl_2$

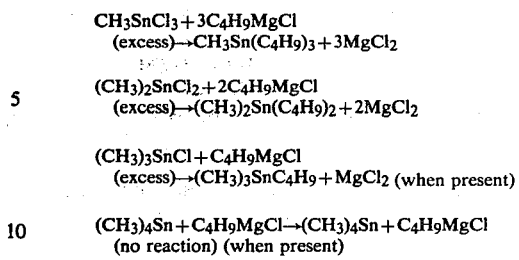

$(CH_3)_3SnCl + C_4H_9MgCl$
(excess) $\rightarrow (CH_3)_3SnC_4H_9 + MgCl_2$ (when present)

$(CH_3)_4Sn + C_4H_9MgCl \rightarrow (CH_3)_4Sn + C_4H_9MgCl$
(no reaction) (when present)

This technique detects and measures tetramethyltin and trimethyltin compounds when present in concentrations as low as 0.1% by weight, and when applied to products prepared by the process of this invention demonstrates that no detectable amounts of these objectionable impurities are formed.

The process according to this invention is complete when the stannic chloride has been consumed, or when analysis of the reaction mixture shows no further change in composition. Surplus stannic chloride can be stripped from the product by brief application of a vacuum, and the residual product is then ready for use, as for example in the preparation of a methyltin mercaptide stabilizer for vinyl chloride polymers, with no further purification.

The proportions of dimethyltin dichloride and stannic chloride that are reacted in the process of this invention can be varied depending on the intended composition of the reaction product, i.e. the desired relative proportions of monomethyltin trichloride to dimethyltin dichloride. The latter proportions, in turn, are determined by the intended use of the product mixture, as for example in the manufacture of a mixed methyltin trimercaptide and dimethyltin dimercaptide stabilizer for vinyl chloride polymers. To illustrate, there are tabulated below the molar proportions of dimethyltin dichloride and stannic chloride required to prepare a series of vinyl chloride polymer stabilizers containing methyltintris(isooctyl thioglycolate) and dimethyltin-bis(isooctyl thioglycolate), based on the sequence of reactions.

$(CH_3)_2SnCl_2 + SnCl_4 \longrightarrow (CH_3)_2SnCl_2 + 2 CH_3SnCl_3$
(excess) (remainder)

$(CH_3)_2SnCl_2 + 2 HSCH_2CO_2C_8H_{17} + 2 NaOH \longrightarrow$ $(CH_3)_2Sn(SCH_2CO_2C_8H_{17})_2 + 2 NaCl + H_2O$
"D"

$CH_3SnCl_3 + 3 HSCH_2CO_2C_8H_{17} + 3 NaOH \longrightarrow$ $CH_3Sn(SCH_2CO_2C_8H_{17})_3 + 3 NaCl + H_2O$
"M"

| "M"/"D" weight ratio | $\dfrac{CH_3SnCl_3}{(CH_3)_2SnCl_2}$ mole ratio | $\dfrac{SnCl_4}{(CH_3)_2SnCl_2}$ mole ratio |
|---|---|---|
| 6:1 | 4.48 | 0.69 |
| 5:1 | 3.74 | 0.65 |
| 4:1 | 2.99 | 0.60 |
| 3:1 | 2.12 | 0.53 |
| 2:1 | 1.45 | 0.43 |
| 3:2 | 1.06 | 0.35 |
| 1:1 | 0.75 | 0.27 |
| 2:3 | 0.50 | 0.20 |
| 1:2 | 0.37 | 0.16 |

-continued $$(CH_3)_2SnCl_2 + SnCl_4 \longrightarrow (CH_3)_2SnCl_2 + 2\,CH_3SnCl_3$$
(excess) (remainder)

$$(CH_3)_2SnCl_2 + 2\,HSCH_2CO_2C_8H_{17} + 2\,NaOH \longrightarrow$$

$$(CH_3)_2Sn(SCH_2CO_2C_8H_{17})_2 + 2\,NaCl + H_2O$$
"D"

$$CH_3SnCl_3 + 3\,HSCH_2CO_2C_8H_{17} + 3\,NaOH \longrightarrow$$

$$CH_3Sn(SCH_2CO_2C_8H_{17})_3 + 3\,NaCl + H_2O$$
"M"

| "M" weight "D" ratio | $\dfrac{CH_3SnCl_3}{(CH_3)_2SnCl_2}$ mole ratio | $\dfrac{SnCl_4}{(CH_3)_2SnCl_2}$ mole ratio |
|---|---|---|
| 1:3 | 0.25 | 0.11 |

Methyltin mercaptide stabilizers as known in the art, which are prepared from mixed methyltin trichloride and dimethyltin dichloride product, can be represented by the formula $(CH_3)_aSn(SR)_{4-a}$, in which a is a 1 or 2 and R is an alkyl group having 8 to 22 carbon atoms, an alkoxycarbonylalkylene group having 1 to 18 carbon atoms in the alkoxy group and 1 to 6 carbon atoms in the alkylene group, or an acyloxyalkylene group having 2 to 22 carbon atoms in the acyloxy group and 2 to 6 carbon atoms in the alkylene group. The methyltin stabilizer so prepared is a mixture of methyltin trimercaptide represented by the formula in which "a" is 1 and dimethyltin dimercaptide represented by the formula in which "a" is 2, i.e. $CH_3Sn(SR)_3$ and $(CH_3)_2Sn(SR)_2$. Representative methyltin stabilizer mixtures prepared in this way include methyltintris(2-ethylhexyl mercaptide) and dimethyltin bis(2-ethylhexyl mercaptide); methyltintris(lauryl mercaptide) and dimethyltinbis(lauryl mercaptide); methyltintris(n-octadecyl mercaptide) and dimethyltinbis(n-octadecyl mercaptide); methyltintris(behenyl mercaptide) and dimethyltinbis(behenyl thioglycolate); methyltintris(methyl 3-mercaptopropionate) and dimethyltinbis(methyl 3-mercaptopropionate); methyltintris(isononyl 3-mercaptopropionate) and dimethyltinbis(isononyl 3-mercaptopropionate); methyltintris(isoamyl 3-mercaptoisobutyrate) and dimethyltinbis(isoamyl 3-mercaptoisobutyrate); methyltintris(n-hexadecyl thioclycolate) and dimethyltinbis(n-hexadecyl thioglycolate); methyltintris(4-acetoxybutyl mercaptide) and dimethyltinbis(4-acetoxybutyl mercaptide); methyltintris(2-(3,5,5-trimethylhexanoyloxy)ethyl mercaptide) and dimethyltinbis(2-(3,5,5-trimethylhexanoyloxy)ethyl mercaptide); methyltintris(2-linoleyloxyethyl mercaptide).

In preparation of a methyltin stabilizer from the methyltin trichloride and dimethyltin dichloride mixture produced by the process of this invention, each mole of methyltin trichloride reacts with 3 moles of mercaptan and 3 equivalents of acid acceptor, and each mole of dimethyltin dichloride reacts with 2 moles of mercaptan and 2 equivalents of acid acceptor, as shown in the following reaction equations, in which for convenience B is used to indicate an equivalent of acid acceptor, and R is as defined above.

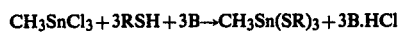
$$CH_3SnCl_3 + 3RSH + 3B \rightarrow CH_3Sn(SR)_3 + 3B.HCl$$

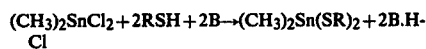
$$(CH_3)_2SnCl_2 + 2RSH + 2B \rightarrow (CH_3)_2Sn(SR)_2 + 2B.HCl$$

Many readily available acid acceptors are suitable, including aqueous and anhydrous ammonia, organic nitrogen bases such as pyridine, triethylamine, and trimethylamine, inorganic bases such as lime, caustic soda and potash, sodium bicarbonate, potassium carbonate, and others. The reaction usually proceeds exothermically and is suitably contriolled to take place between 30° and 75° C. A slight excess of the mercaptan and/or a water-immiscible solvent can be used to assist the separation of the desired methyltin stabilizer from the spent form of the acid acceptor. After separation from the acid acceptor by-product, the preparation of the stabilizer is completed by solvent stripping, drying, or filtration, as required.

EXAMPLE I

A mixture of 660 g (3 moles) dimethyltin dichloride and 470 g (1.8 moles) stannic chloride were charged into a 2-liter 316 stainless steel Paar Series 4500 stirred autoclave equipped with a 2000 psig rupture disc and a 0–1000 psig pressure guage. The mixture was stirred and heated at 220°–229° C. under 57–68 psig for 3½ hours. The product consisted of 73.3% methyltin trichloride and 26.7% dimethyltin dichloride by NMR analysis.

EXAMPLE II

Following the procedure in Example I, a mixture of 660 g (3 moles) dimethyltin dichloride and 196 g (0.75 moles) stannic chloride was stirred and heated at 220°–228° C. under 41–49 psig for 1 hour. The product consisted of 46.5% methyltin trichloride and 53.5% dimethyltin dichloride by NMR analysis.

EXAMPLE III

Following Example I, a mixture of 660 g (3 moles) dimethyltin dichloride and 196 g (0.75 moles) stannic chloride was stirred and heated at 171°–174° C. under 13–16 psig for 18 hours. NMR analysis indicated the product consisted of 40.4% methyltin trichloride and 59.6% dimethyltin dichloride. G C analysis showed that the product contained 0.2% stannic chloride.

Methyltin mercaptide products from the mixed intermediate products of Example I, II, and III were found to be excellent stabilizers for vinyl chloride polymers.

The embodiments of the invention in which an exclusive property or privilege is claimed are defined as follows:

1. In a process of preparing a mixed methyltin mercaptide stabilizer for vinyl chloride polymers in which the weight proportions of monomethyltin trimercaptide to dimethyltin dimercaptide range from 6:1 to 1:3, comprising the steps of treating a mixture of dimethyltin dichloride and monomethyltin trichloride with a mercaptan and an acid acceptor, and recovering the stabilizer mixture of monomethyltin trimercaptide and dimethyltin dimercaptide, the improvement wherein said mixture of dimethyltin dichloride and monomethyltin trichloride is prepared by heating dimethyltin dichloride with 0.1 to 0.7 molar proportion of stannic chloride in the absence of catalyst, without further purification.

2. Process according to claim 1 in which the monomethyltin trimercaptide and dimethyltin dimercaptide are represented by the respective formulae $CH_3Sn(SR)_3$ and $(CH_3)_2Sn(SR)_2$ in which R is an alkyl group having 8 to 22 carbon atoms, an alkoxycarbonylalkylene group having 1 to 18 carbon atoms in the alkoxy group and 1 to 6 carbon atoms in the alkylene group, or an acyloxyalkylene group having 2 to 22 carbon atoms in the acyloxy group and 2 to 6 carbon atoms in the alkylene group.

3. Process according to claim 2 in which R in each of the formulae $CH_3Sn(SR)_3$ and $(CH_3)_2Sn(SR)_2$ is $-CH_2CO_2C_8H_{17}$, $C_8H_{17}$ being isooctyl.

* * * * *